(12) United States Patent
Dutreux et al.

(10) Patent No.: US 8,574,645 B2
(45) Date of Patent: Nov. 5, 2013

(54) ANTIMICROBIAL COMPOSITION

(75) Inventors: Nicole Liliane Dutreux, Delft (NL); Ben Rudolf De Haan, Voorburg (NL); Jacobus Stark, Rotterdam (NL)

(73) Assignee: DSM IP Assets B.V., Te Heerlen (NL)

( * ) Notice: Subject to any disclaimer, the term of this patent is extended or adjusted under 35 U.S.C. 154(b) by 894 days.

(21) Appl. No.: 11/663,347

(22) PCT Filed: Sep. 19, 2005

(86) PCT No.: PCT/EP2005/054663
§ 371 (c)(1), (2), (4) Date: Mar. 21, 2007

(87) PCT Pub. No.: WO2006/032646
PCT Pub. Date: Mar. 30, 2006

(65) Prior Publication Data
US 2007/0264394 A1 Nov. 15, 2007

(30) Foreign Application Priority Data

Sep. 23, 2004 (EP) .................................... 04104633
Mar. 8, 2005 (EP) .................................... 05101792
Apr. 26, 2005 (EP) .................................... 05103375

(51) Int. Cl.
*A23L 1/00* (2006.01)
*A23L 3/3463* (2006.01)

(52) U.S. Cl.
USPC ........................................... 426/89; 426/335

(58) Field of Classification Search
USPC ........................................... 426/89, 326, 321
See application file for complete search history.

(56) References Cited

U.S. PATENT DOCUMENTS

| | | | |
|---|---|---|---|
| 5,552,151 A | 9/1996 | Noordam et al. | |
| 5,597,598 A | 1/1997 | Van Rijn et al. | |
| 5,738,888 A | 4/1998 | Cirigliano et al. | |
| 5,773,062 A | 6/1998 | Cirigliano et al. | |
| 5,821,233 A | 10/1998 | Van Rijn et al. | |
| 5,895,680 A | 4/1999 | Cirigliano et al. | |
| 5,962,510 A | 10/1999 | De Haan et al. | |
| 5,997,926 A | 12/1999 | Van Rijn et al. | |
| 6,146,675 A | 11/2000 | Cirigliano et al. | |
| 6,150,143 A | 11/2000 | Raghoenath et al. | |
| 6,228,408 B1 | 5/2001 | Van Rijn et al. | |
| 6,369,036 B1 | 4/2002 | Van Rijn et al. | |
| 6,655,081 B1 | 12/2003 | Stark et al. | |
| 7,816,332 B2 | 10/2010 | Stark et al. | |
| 2001/0046538 A1 | 11/2001 | Bunger et al. | |
| 2003/0087003 A1 | 5/2003 | Ang .............................. | 426/61 |

FOREIGN PATENT DOCUMENTS

| | | |
|---|---|---|
| CN | 1280774 | 1/2001 |
| CN | 1336145 A | 2/2002 |
| CN | 1593210 A | 3/2005 |
| EP | 0 608 241 A | 8/1994 |
| EP | 0 608 944 A1 | 8/1994 |
| EP | 0 678 241 A1 | 10/1995 |
| EP | 1 608 808 A | 1/2001 |
| WO | WO 03/070026 A1 | 2/2003 |

OTHER PUBLICATIONS

International Search Report and Written Opinion mailed Jan. 19, 2006 in PCT/EP2005/054663.
Stark (1995), Penicillium discolor. Symposiumbook "Voorkoming van ongewenste schimmelgroei op kaas": 15-18. (Article in Dutch).
Stark (1997), Moulds in cheese industry. Abstract book "World Congress on Food Hygiene". (lecture on symposium; Article in Dutch).
Frisvat et al. (1997), Penicillium discolor, a new species from cheese nuts and vegetables. Antonie van Leeuwenhoek 72:119-126.
Stark (1997), Schimmelbestrijding in de Nederlandse kaasindustrie. De Ware(n)-Chemicus 27: 173-176. (Article in Dutch).
Van Rijn et al. (1997), Penicillium discolor in de Nederlandse kaasindustrie. Voedingsmiddelentechnologie 30:19-23. (Article in Dutch).
Hoekstra et al. (1998), Survey of the fungal flora in Dutch cheese factories and warehouses. Journal of Food Mycology 1:13-22.
Stark (1999), Natamycine en schimmelproblemen in de kaasindustrie. Abstract book symposium "Resistentieproblematiek en ecologie van voedselgerelateerde micro-organismen". (Article in Dutch).
Stark (1999), Permitted preservatives—Natamycin. Encyclopedia of Food Microbiology (Academic Press, ed. Robinson et. al) vol. 3:1776-1781. (Review).
Dutreux et al. (2003), Growth prevention of mycotoxin-forming moulds on food products using Delvocid®. Poster presented at the seconds world mycotoxin forum in Noordwijk (Feb. 17-18, 2003).
Stark (2003), Natamycin, an effective fungicide for food and beverages. In: Natural antimicrobials for the minimal processing of foods. (Woodhead Publishing in Food Science and Technology, ed. S. Roller):82-97. (Review).
Stark and Tan (2003). Natamycin. In: Food Preservatives 2nd edition (Kluwer Academic, ed. G. Gould):179-195. (Review).
Stark (2007). How can I protect my food with a preservative? In: Food Mycology 2007: emerging mold problems and spoilage in food and beverages (Ed. R. A Samson et. al.):19.
Stark (2007). Cheese and fermented sausages. In: Food Mycology, a multifaceted approach to fungi and food (CRC Press, ed. J. Dijksterhuis and R.A. Samson). V25: 319-331. (Review).

(Continued)

*Primary Examiner* — D. Lawrence Tarazano
*Assistant Examiner* — Katherine Deguire
(74) *Attorney, Agent, or Firm* — Miles & Stockbridge, PC.

(57) ABSTRACT

The present invention describes a process to preserve a water-containing product such as a foodstuff, which comprises adding natamycin and nisin to the product, whereby at least 90% (w/v) of natamycin is dissolved and/or less than 10% (w/v) of natamycin is present in crystal form.

24 Claims, No Drawings

(56) References Cited

OTHER PUBLICATIONS

Stark, J. et al., Chapter 5, "Natamycin: an effective fungicide for food and beverages", Natural antimicrobials for the minimal processing of foods, CRC Press, p. 82-97 (2003).
Russel, N.J. et al., Food Preservatives, 2nd Edition, p. 180-181 (2003).
Reps, A. et al., Pakistan Journal of Nutrition, 1(5):243-247 (2002).
Holley, R. et al., "Effect of Sorbate and Pimaricin on Surface Mold and Ripening of Italian Dry Salami", Food Research Contribution, vol. 19, No. 1 (1986).
Opposition by Dupont Nutrition Bioscience APS EP 1793692 "Antimicrobial Composition" in the name of DSM IP Assets B.V., Aug. 13, 2013.
Notice of opposition to a European patent; Patent No. EP1793692/ Application No. EP05787302.8, Aug. 13, 2013; DSM IP Assets B.V.

ANTIMICROBIAL COMPOSITION

This application is the US national phase of international application PCT/EP2005/054663 filed 19 Sep. 2005 which designated the U.S. and claims benefit of EP 04104633.5; EP 05101792.9; EP 05103375.1, dated 23 Sep. 2004; 8 Mar. 2005; 26 Apr. 2005, respectively the entire content of which is hereby incorporated by reference.

FIELD OF THE INVENTION

The present invention discloses a method to prevent or delay microbial growth in or on foodstuffs, agricultural products, pharmaceutical products and cosmetics. More specifically the method comprises using as an ingredient or applying to a food surface an anti-microbial composition including natamycin as anti-fungal agent and nisin as anti-bacterial agent.

BACKGROUND OF THE INVENTION

The need for improved food preservation methods is great. It has been estimated that about one quarter of the word's food supply is lost as a result of microbial spoilage and food-borne microbial infections represent a constant and serious threat to human health.

Several bacterial species that may contaminate and grow in foodstuffs and crops are pathogenic or produce toxins and cause a range of food-poisoning diseases. Despite substantial improvement in the technology and hygiene, food products may be exposed to spoilage and pathogenic bacteria in the food-handling environment and the number of food poisoning is still increasing in most of the countries.

Fungal spoilage can lead to serious economic losses. Several food products e.g. agricultural products, dairy and meat products, fruits and vegetables and derived products, bakery products and cosmetics are very susceptible to fungal growth. Examples of dairy products are cheese, cottage cheese, ricotta and yogurt. Dried cured sausages are an example of meat products. Examples of agricultural products are crops such as cereals, nuts, fruits, vegetables and flower bulbs. Spoilage by fungi does not only affect the quality of the product, but also represents a health risk. It is well known that some fungal species, which grow on e.g. dairy products and sausages, can produce mycotoxins. Some mycotoxins are extremely dangerous as they can cause lethal diseases. Therefore the outgrowth of unwanted fungi in and on food products should always be prevented.

Food preservation techniques, e.g. heat processing, freezing, ultrasound, irradiation, and modified atmosphere packaging, significantly reduce microbial load but of particular concern is the evidence that processed foods are being contaminated with microorganisms following processing and prior to packaging. Of rinsing concern in the food industry is microbial spoilage of various foods such as dairy and meat products, dressings, spreads, margarines and seafood. Especially food products in the 2.0 to 7.0 pH range are known to be susceptible to microbial spoilage by yeast, mould, acid tolerant bacteria and/or mesophilic or thermophilic spore forming and non-spore forming bacteria.

Mostly, processed foods are not eaten directly after processing thereby permitting bacteria, yeast or mould introduced by post-contamination to grow. Since food consumption may occur without reheating the processed foods to sufficient temperatures for sufficient time, there is a risk of food poisoning or food spoilage. Furthermore, the recent trend for minimally processed foods with the intrinsic nutritional and sensory qualities of raw and fresh foods has raised a new safety risk. Milder preservation treatments, such as high hydrostatic pressure and pulsed electric fields have been proved to be successful but rely on effective hurdles i.e. cold chain and addition of natural anti-microbials.

There has been extensive research conducted in the field of food safety to develop effective anti-microbial compositions, which function as anti-fungal and anti-bacterial compositions.

In U.S. Pat. No. 5,895,680 by Cirigliano et al., the preservative system including natamycin and nisin is stated. The instability of aqueous natamycin solution is compensated by increased natamycin concentrations. In U.S. Pat. No. 5,895,680 it is taught that natamycin has to be present in amount of at least 1.5 times the maximum solubility based on the water content present in the foodstuff. The reason behind this is that it is believed that soluble natamycin is not stable in aqueous surroundings and that therefore always solid (for example crystal or amorphous) natamycin has to be present for the anti fungal activity.

DESCRIPTION OF THE INVENTION

The object of this invention is to provide a novel natural microbiocidal and/or microbiostatic composition and a method for preserving foodstuffs, agricultural goods, cosmetics and pharmaceutical products by employing a novel combination of microbiocidal and microbiostatic components in or on the foodstuffs. The above subject may be achieved by incorporating a combination of polyene antifungal agent and a bacteriocin into foodstuffs and/or by treating the surface of foodstuffs with the novel composition of polyene and bacteriocin.

The polyene antifungal agent may be, for example, natamycin, lucensomycin, nystatin or amphotericin. Examples of bacteriocins are nisin, pediocin, reuterin and sakacin. According to one aspect of this invention the polyene antifungal agent is natamycin. A preferred embodiment of the invention is the combination of natamycin with nisin or pediocin.

In a first aspect of the invention, there is provided a process to preserve products, such as food products, which comprises applying in or on said product an anti-microbial composition including natamycin and nisin.

According to a first preferred embodiment, the invention relates to a process to preserve a water-containing product such as a food product, which comprises applying in the product an anti-microbial composition including natamycin and nisin, whereby at least 90% (w/v) of natamycin is dissolved and/or less than 10% (w/v) of natamycin is present in solid form. Preferably, at least 95% (w/v) of natamycin is dissolved and/or less than 5% (w/v) of natamycin is present in solid form. More preferably, at least 97% (w/v) of natamycin is dissolved and/or less than 3% (w/v) of natamycin is present in solid form. Most preferably, almost all natamycin is dissolved and almost no natamycin is present in solid form.

The total amount of natamycin present is either dissolved in water or present in a solid form. Solid form of natamycin means 'natamycin not dissolved in water'. The solid form of natamycin may preferably comprise natamycin particles. Natamycin particles are natamycin crystals, which, for example, may have the following forms: needle-formed crystals, disc-formed crystals or the like. The natamycin particles usually have diameters ranging from 0.5-20 micrometer. The diameter of the natamycin particle is the largest distance from one part of the particle to the other end of the particle. Needle-formed natamycin particles with diameters of more than 40 micrometer have been observed. Diameters may be determined using a microscope. Preferably, natamycin particles have an average particle diameter of at least 2 micrometer, more preferably the natamycin particles have an average particle diameter of at least 5 micrometer and most preferably the natamycin particles have an average particle diameter of at least 10 micrometer. The presence of solid form of natamycin may be determined by microscopy.

Throughout the application, natamycin concentration is measured using the International Dairy Federation (IDF) Standard 140A:1992. Nisin concentration is measured using the well-known agar diffusion test.

Nisin is a peptide-like antibacterial substance produced by microorganisms such as *Lactococcus lactis* subsp. *lactis*. It is active against gram-positive bacteria. Nisin is non-toxic and is free of side effects. Nisin is a Generally Recognized as Safe substance and is widely used in a variety of foods. Examples of such products are processed cheese, milk, clotted cream, dairy desserts, ice cream mixes, liquid egg, hot-baked flour products, dressings and beer. Nisin is heat-stable and can stand sterilization temperatures with minimal loss of activity. The World Health Organization Committee on Biological Standardization has established an international reference preparation of nisin, and the international unit (IU hereinafter) is defined as 0.001 mg of this preparation. Delvoplus® and Nisaplin®, brand names for a nisin concentrate containing 1 million IU per gram, are distributed by DSM and Danisco, respectively. Effective levels of nisin to preserve food products range from 10 to 800 IU/g or 0.25 to 20 ppm of nisin.

Natamycin has been used for more than 30 years to prevent outgrowth of fungi on cheeses and sausages. Natamycin is on the market under the brand name of Delvocid® or Natamax®, a powder composition containing 50% (w/w) of natamycin and 50% (w/w) of lactose. Natamycin has a MIC (Minimal Inhibition Concentration) of less than 10 ppm for most food born fungi while its solubility in water is from 30 to 50 ppm. Natamycin can easily be applied to prevent spoilage by fungi in food products. However, the low solubility of natamycin has limited its use to the surface treatment of cheese and fluids e.g juices, lemonades, wine and yoghurt. Surprisingly we found natamycin, when introduced into foodstuffs at concentrations whereby almost no crystal form or solid form of natamycin is present for example in concentrations ranging from 120 ppm, based on the water content of the product wherein it is used, to be extremely effective against yeast and mould, completely inhibiting or significantly delaying their outgrowth. Natamycin can be added as solid, suspension on any of other form to a water-containing product in an amount such that all natamycin will dissolve. Surprisingly we have found that natamycin dissolved in water-containing product for example food products and preferably in dairy products, is stable while in literature it is mentions that dissolved natamycin in water is unstable.

According to a preferred embodiment, the process of the invention is applied to a food product, which is a water-containing product, wherein natamycin and nisin are present in the product and wherein natamycin is present in an amount of about 1 to 20 ppm natamycin based on the water content of the product, preferably about 1 to 15 ppm. Preferably, an amount of about 0.25 to 20 ppm of nisin is present in the product, more preferably about 1 to 15 ppm of nisin.

According to a second preferred embodiment, the process of the invention is a process for preserving a product such as a food product, which comprises applying on the product an anti-microbial composition including natamycin and nisin, whereby natamycin is present in an amount ranged between 0.01 and 10 ppm. More preferably, nisin is present in an amount ranged between 0.0001 and 1 ppm.

Applying the anti-microbial composition on the product means, applying it on the surface of the product. The surface of a product, such as a food product is defined as being the outside layer of the product, which may be in contact with oxygen. For example if the food product is cheese, the cheese surface is the outside layer of cheese or parts of cheese, even in the sliced, shredded or grated form. The term cheese surface includes the outside of the whole cheese, disregarding whether a ring has been formed or not.

Surprisingly, we found that natamycin and nisin, when applied at the surface of product such as a food product in concentrations ranging from 0.01 to 10 ppm for natamycin and 0.0001 and 1 ppm for nisin were found both extremely effective against yeast and mould for natamycin and Gram positive bacteria for nisin, completely inhibiting or significantly delaying their outgrowth.

Nisin and natamycin may be added separately or at the same time to the product. This addition may be performed simultaneously or subsequently. According to a preferred embodiment, nisin and natamycin are added at the same time to the product.

An anti-microbial composition comprising natamycin and nisin is preferably added to the product after the reduction of size has occurred at the end of the processing. More preferably, the anti-microbial composition is added at the end of the processing before packaging.

The anti-microbial compositions according to the invention, which may be used for the treatment of food product such as cheese or sausages may be, for example, liquids for treatment by immersion or dipping and/or by spraying, or coating emulsions like that of the polyvinyl acetate type or of the oil in water (o/w) or water in oil (w/o) type.

Anti-microbial compositions of the invention for the treatment of agricultural products such as flower bulbs, (kernel) grain and vegetables may be, for example, aqueous systems which may be used by methods known per se, e.g. dipping or spraying.

Examples of pharmaceutical compositions for topical application in which a solution of the anti-microbial composition of the invention may be incorporated are lotions, creams and ointments.

The amount of fungicide, e.g. natamycin, in a liquid composition for immersion treatment may be from 0.001% to 2% w/w. Preferably, the amount is from 0.01% to 1% w/w. The amount of nisin, in a liquid composition for immersion treatment may be from 0.0001 to 1% w/w. Preferably the amount of nisin is from 0.001 to 1% w/w, more preferably from 0.01 to 0.05% w/w. In principle, the immersion liquid may be of any kind. When an aqueous system is used, the addition of a surfactant may be of advantage, in particular for treating objects with a hydrophobic surface.

In a coating emulsion according to the invention, the amount of fungicide, e.g. natamycin, may be from 0.001% to 2% w/w, preferably from 0.01% to 1% w/w and more preferably from 0.01% to 0.5% w/w. The amount of nisin, in a coating emulsion may be from 0.0001 to 1% w/w. Preferably the amount of nisin is from 0.001 to 1% w/w, more preferably from 0.01 to 0.05% w/w. The coating emulsion may be of the o/w or w/o type. Particularly preferred are emulsions prepared from coating emulsions commonly employed in the food industry. For example, for the treatment of hard cheeses an aqueous polymer emulsion of the polyvinyl acetate type may be used.

A composition comprising natamycin and nisin can be added to the product at any moment or step of the processing.

Natamycin and nisin can be added in combination or separately, in the end product before packaging, during processing or in any ingredients used to prepare the products. The advantage of the present invention is that it allows the production of microbiologically stable and safe foodstuffs products with low concentration of anti-microbials. The innovative composition can be used to preserve microbiological safety and/or stability in all kind of food products such as dairy products, ice cream mixes, hot-baked flour products, spreads, margarines, sauce, dressings or any other foodstuffs distributed at ambient or chilled temperatures. Preferred food products have pH ranging from pH 2 to pH 7.0. Preferred food products are dairy products and more especially cottage cheese, ricotta, cream cheese, sour cream and dairy desserts. The addition of natamycin and nisin to food products is furthermore expected to reduce or completely eliminate moulds, yeasts and bacterial outgrowth on the food products in the time frame comprised between the end of the processing of the product, size reduction included and commercial sale. This time frame varies with the type of food, the distribution and sale conditions. Preferably, the product to be treated is such that its surface will be in contact with oxygen at the end of its processing and/or later on if a reduction of size occurs. Preferably the product is a food product such as dairy products, ice cream mixes, hot-baked flour products, spreads, margarines, sauce, dressings or any other food product distributed at ambient or chilled temperatures.

According to another preferred embodiment, the anti-microbial composition of the invention comprising natamycin and nisin has a pH ranging from pH 2 to pH 7.0, more preferably from 3 to 5. According to another preferred embodiment, the anti-microbial composition of the invention further comprises water and/or salt and/or any component selected from the group consisting of a solvent, a surfactant, a carrier, a food acid, a thickener such as xanthan, any other food grade anti-microbial compound. Preferred solvents, surfactants and carrier are already described in WO 95/08918. Preferred thickeners were described in U.S. Pat. No. 5,962,510 and U.S. Pat. No. 5,552,151. Preferred food acids such as an organic acidic anti-fungal agent and/or any additional acid are described in EP 608 944 B1. The content of the patents and patent applications cited in this paragraph is fully incorporated by reference in this context.

According to a second aspect of the invention, there is provided a product, such as a food product comprising an anti-microbial composition including natamycin and nisin.

According to a first preferred embodiment, the product is a water-containing product such as a food product, which comprises an anti-microbial composition including natamycin and nisin, whereby at least 90% (w/v) of natamycin is dissolved and/or less than 10% (w/v) of natamycin is present in solid form. Preferably, at least 95% (w/v) of natamycin is dissolved and/or less than 5% (w/v) of natamycin is present in solid form. More preferably, at least 97% (w/v) of natamycin is dissolved and/or less than 3% (w/v) of natamycin is present in solid form. Most preferably, almost all natamycin is dissolved and almost no natamycin is present in solid form.

Preferably, natamycin is present in the product in an amount of 1 to 20 ppm based on the water content of the product, more preferably natamycin is present in an amount ranged between 0.01 and 10 ppm. According to another preferred embodiment, the product comprises 0.25 to 20 ppm of nisin, more preferably nisin is present in an amount ranged between 0.0001 and 1 ppm.

According to a second preferred embodiment, natamycin and nisin are present at the surface of the product. Preferably, natamycin is present in an amount ranged between about 0.01 and 10 ppm. Preferably natamycin is present in an amount ranged between about 0.05 and 7 ppm, even more preferably about 0.1 and 5 ppm and most preferably about 0.5 ppm and 4 ppm. According to another preferred embodiment, nisin is present in an amount ranged between about 0.0001 and 1 ppm, more preferably about 0.0005 and 0.75 ppm, even more preferably about 0.001 and 0.5 ppm, even more preferably about 0.005 and 0.5 ppm and most preferably about 0.007 and 0.4 ppm.

According to a third aspect of the invention, there is provided the use of natamycin to obtain a product, such as a food product comprising an anti-microbial composition including natamycin and nisin.

According to a first preferred embodiment of the invention, the invention relates to the use of natamycin to obtain a water-containing product, such as a food product comprising an anti-microbial composition including natamycin and nisin, whereby at least 90% (w/v) of natamycin is dissolved and/or less than 10% (w/v) of natamycin is present in solid form. The product has been defined earlier in the description.

According to a second preferred embodiment, natamycin and nisin are applied at the surface of the product.

Before, during or after the addition of natamycin and nisin to the product, other ingredients such as colorants, texturals etc. can be added as well to the product.

The invention will further now be illustrated by examples, which should not be construed as limiting the scope of the invention.

EXAMPLES

Example 1

Natamycin Stability in Cottage Cheese

This example describes the stability of low natamycin concentration in cottage cheese containing nisin versus a lower stability in water with similar pH.

Cottage cheese was prepared following the standard procedure for cottage cheese making. The dry curd was obtained by addition of a starter culture to pasteurized skim milk. After acidification till pH 4.4 the curd was pasteurized and rinsed with water. The dry curd was mixed with the dressing at the ratio 66% curd and 44% dressing. Before mixing the curd and the dressing, the preservatives Delvocid® and Delvoplus® were added to the dressing. The preservative concentrations in the end products were 2.5 and 5 ppm of natamycin (5 and 10 ppm of Delvocid®) and 1.25 and 2.5 ppm of nisin (50 and 100 ppm of Delvoplus®). The moisture content of cottage cheese (dry curd mixed with the dressing) was 82%.

The procedure described in the International IDF (International Dairy Federation) Standard 140A:1992 for cheese was used to determine the concentration of natamycin in the cottage cheese samples. In total 12 different samples were analysed in triplicate. The remaining percentage of natamycin was calculated using the average of the triplicate. The results presented in Table 1 show that natamycin was stable in cottage cheese. After 6 weeks of storage at refrigerated temperature, the average stability of natamycin in cottage cheese was of 92%.

TABLE 1

Stability of natamycin in cottage cheese stored at 4-7° C.

|  | 0 week | 3 weeks | 6 weeks |
|---|---|---|---|
| Remaining | 100 | 96 | 86 |
| percentage | 100 | 94 | 89 |
| of natamycin | 100 | 88 | 97 |
|  | 100 | 103 | 92 |
|  | 100 | 96 | 88 |
|  | 100 | 102 | 91 |
|  | 100 | 98 | 93 |
|  | 100 | 99 | 90 |
|  | 100 | 99 | 93 |
|  | 100 | 100 | 97 |
|  | 100 | 97 | 87 |
|  | 100 | 96 | 98 |
| Average | 100 | 98 | 92 |

Example 2

Antifungal Activity of Low Natamycin Concentration in Cottage Cheese Containing Nisin This example describes the antifungal activity of low natamycin concentration (2.5 and 5 ppm) in cottage cheese, in presence of nisin. Cottage cheese was prepared as described above. After adding the dressing to the dry curd, the cottage cheese was inoculated with yeasts and fungal cells, *Kluyveromyces marxianus* CBS 1557 and *Penicillium roqueforti* CBS 304.97, respectively. Following the artificial contamination, natamycin and/or nisin was added to the cottage cheese at two different concentrations, 2.5 and 5 ppm for natamycin and 1.25 and 2.50 ppm for nisin. The antifungal activity of natamycin against the yeast and the mould cells was evaluated after 3 and 6 weeks of incubation at 4° C. through the enumeration of the viable cells in the inoculated samples, in presence or not of preservatives. The number of viable yeast of fungal cells was also determined in a negative sample, non inoculated cottage cheese without preservatives and in a positive control, sample artificially contaminated with yeast and fungal cells without preservative. The results are presented in the tables 2 and 3. It is clear that natamycin present at 2.5 or 5 ppm was effective in preventing the growth of *K. marxianus* and *P. roqueforti* for up to 6 weeks at 4-7%.

TABLE 2

Antifungal activity against *Kluyveromyces marxianus* CBS 1557 of natamycin in presence or absence of nisin, after 0, 3 and 6 weeks of incubation at 4-7° C.

| Concentration (ppm) | | Log CFU/g of *K. marxianus* | | |
|---|---|---|---|---|
| Natamycin | Nisin | 0 week | 3 weeks | 6 weeks |
| 0.00 | 0.00 | 1.80 | 3.50 | 4.50 |
| 2.50 | 0.00 | 1.70 | 1.70 | <1.00 |
| 2.50 | 1.25 | 2.00 | 0.80 | <1.00 |
| 2.50 | 2.50 | 1.90 | 0.80 | <1.00 |
| 5.00 | 0.00 | 1.30 | <1.00 | <1.00 |
| 5.00 | 1.25 | 1.90 | 1.10 | <1.00 |
| 5.00 | 2.50 | 1.70 | <1.00 | <1.00 |

TABLE 3

Antifungal activity against *Penicillium roqueforti* CBS 304.97 of natamycin in presence or absence of nisin, after 0, 3 and 6 weeks of incubation at 4-7° C.

| Concentration (ppm) | | Log spores/g of *P. roqueforti* | | |
|---|---|---|---|---|
| Natamycin | Nisin | 0 week | 3 weeks | 6 weeks |
| 0.00 | 0.00 | 1.80 | 2.70 | 5.40 |
| 2.50 | 0.00 | 1.70 | 1.70 | <1.00 |
| 2.50 | 1.25 | 1.60 | <1.00 | <1.00 |
| 2.50 | 2.50 | 1.60 | <1.00 | <1.00 |
| 5.00 | 0.00 | 1.60 | <1.00 | <1.00 |
| 5.00 | 1.25 | 1.60 | <1.00 | <1.00 |
| 5.00 | 2.50 | 1.70 | <1.00 | <1.00 |

Example 3

Antibacterial Activity of Nisin in Cottage Cheese Containing Low Natamycin Concentration This example describes the antibacterial activity of nisin (1.25 and 2.5 ppm) in cottage cheese, in presence of low natamycin concentration. Cottage cheese was prepared as described above. After adding the dressing to the dry curd, the cottage cheese was inoculated with yeasts, fungal cells and cells of *Listeria innocua* LM35. Following the artificial contamination, the cottage cheese was added with two nisin concentrations 1.25 and 2.5 ppm and/or in combination with natamycin at the concentration 2.5 or 5 ppm. The antibacterial activity of nisin against *L. innocua* was evaluated after 3 and 6 weeks of incubation at 4° C. through the enumeration of the viable cells in the inoculated samples, in presence or not of preservatives. The number of viable bacterial cells was also determined in a negative sample, non inoculated cottage cheese without preservatives and in a positive control, sample artificially contaminated with bacteria.

The results presented in the table 4 indicate that nisin inhibited the growth of *L. innocua* in presence or not of natamycin.

TABLE 4

Antifungal activity against *Listeria innocua* LM 35 of natamycin in presence or absence of nisin, after 0, 3 and 6 weeks of incubation at 4-7° C.

| Concentration (ppm) | | Log CFU/g of *L. innocua* | | |
|---|---|---|---|---|
| Natamycin | Nisin | 0 week | 3 weeks | 6 weeks |
| 0.00 | 0.00 | 2.00 | 3.10 | 6.30 |
| 2.50 | 0.00 | 1.90 | 2.50 | 4.50 |
| 2.50 | 1.25 | 2.00 | <1.00 | <2.00 |
| 2.50 | 2.50 | 1.90 | <1.00 | <1.00 |
| 5.00 | 0.00 | 1.90 | 1.90 | 4.70 |
| 5.00 | 1.25 | 1.60 | <1.00 | <1.00 |
| 5.00 | 2.50 | 2.10 | <1.00 | <1.00 |

Material and Methods Used in Coming Examples

Non-contaminated brine was obtained from the Food Innovation Centre of DSM Food Specialties, P.O. Box 1, 2600 MA, Delft, The Netherlands.

Freshly made 2 kg brined wheels of Gouda cheeses were obtained from the Food Innovation Centre of DSM Food Specialties, P.O. Box 1, 2600 MA, Delft, The Netherlands. The contamination of the cheeses was tested by evaluating the presence of yeast cells of the type *Debaromyces hansenii* ATCC 10623) and by the presence of *Lactobacillus* salt-resistant strains, which are both normally found in brine baths. In this example, *Lactobacillus sakei* ATCC 15521 was used.

The source of natamycin used in the anti-microbial composition is Delvocid®, containing 50% active (w/w) natamycin, DSM Food Specialties, P.O. Box 1, 2600 MA, Delft, The Netherlands.

The source of nisin used in the anti-microbial composition is Delvoplus®, containing 2.5% active (w/w) nisin, DSM Food Specialties, P.O. Box 1, 2600 MA, Delft, The Netherlands.

Sodium chloride (NaCl) was purchased by Gaches Chimie France, 31750 Escalquens, France.

Example 4

Preparation of Several Anti-Microbial Compositions

This example describes a method to prepare several dipping anti-microbial compositions suitable for use as a food coating to prevent microbial growth on cheese. These anti-microbial compositions were prepared by adding 1 gram of Delvocid® and/or 0.5 gram of Delvoplus® with 100 gram of NaCl to 800 ml of tapwater. 0.2% xanthan was further added. The pH of the composition was adjusted to 4.5 by adding citric acid. The different ingredients were homogenized used an electric top stirrer (type RW 20 DZM, from Janke & Kunkel equipped with a Ruston stirrer). Finally the weight of the mixture was adjusted to one kilo by addition of tap water. The final compositions were stored at 18° C. in the dark. Three anti-microbial compositions have been prepared:
  one containing 500 ppm natamycin
  one containing 12.5 ppm nisin
  one containing 500 ppm natamycin and 12.5 ppm nisin: anti-microbial composition of the invention Example 5

Method for Testing the Efficacy of the Anti-Microbial Compositions

This example describes the method used to test the efficacy of the compositions, described in example 4, to protect cheeses contaminated from the brine. A freshly brined wheel of Gouda cheese was dipped in a brine solution containing $10^6$ CFU per ml of the salt resistant yeast *Debaromyces hansenii* ATCC 10623 and/or $10^4$ CFU per ml of salt-resistant *Lactobacillus sakei* ATCC 15521 for one minute and accordingly flushed with tap water and accordingly dipped in the compositions as described in example 4.

Five samples of cheese were used for each anti-microbial composition tested. The cheese contained:
  2.5 ppm natamycin or
  0.06 ppm nisin or
  2.5 ppm natamycin and 0.06 ppm nisin (composition of the invention) or
  no anti-microbial compound in the composition (control)

The cheeses were accordingly vacuum packed in standard polyethylene (PE) bags with a Kramer & Grebe compack machine and stored at 18° C. in the dark until the moment of analysis.

The efficacy of the different compositions was expressed as the difference between the amount of yeasts and lactobacilli found on the surface of the different tested cheeses and the determined surface contamination for the control cheese. The control cheese is a contaminated cheese coated with a composition, which does not contain any anti-microbial compound.

Example 6

Determination of the Contamination Levels on the Cheese Surface after Removal of the Protection Foil For each five tested cheese, 20 g of cheese were sampled from the total cheese surface and suspended with 180 ml of citrate buffer at 45° C. Following homogeneization, 1 ml of cheese suspension was further diluted in physiological salt and plated out on specific agar, OGY (oxytetracycline yeast extract)+4% NaCL for the yeast and TGV (tryptone glucose meat extract)+4% NaCl, for the lactobacilli. The plates were incubated for 3 days at 30° C. for the yeast and 37° C. for the lactobacilli.

Example 7

Anti-Microbial Efficacy of the Different Compositions

Anti-microbial compositions were prepared as described in example 4 and tested according to example 5. The cheeses were stored for 3 months between 6 and 10° C. and the contamination levels for each cheese were determined following the method of the example 6. The results are listed in the table below.

TABLE 5

| Average contamination levels (expressed in CFU/cm2) | | | | | |
| --- | --- | --- | --- | --- | --- |
| Average contamination level in cfu's/cm² | No anti-microbial treatment t = 0 | No anti-microbial treatment t = 3 months | Treatment with Delvocid (2.5 ppm natamycin) | Treatment with Delvoplus (0.06 ppm nisin) | Treatment with Delvocid and Delvoplus (2.5 ppm natamycin and 0.06 ppm nisin) |
| Yeast | $10^4$ | $10^6$ | 0 | $10^6$ | 0 |
| Lactobacilli | $10^2$ | $10^3$ | $10^4$ | 0 | 0 |

The invention claimed is:

1. A process to preserve a water-containing food product comprising at least about 82% moisture content, the process comprising the step of applying natamycin and nisin in or on the product, wherein:
  (a) if natamycin and nisin are applied in the product, then
    (ia) natamycin is present in the product in an amount of 1 to 10 ppm natamycin based on the water content of the product, wherein at least 90% (w/v) of natamycin is dissolved and/or less than 10% (w/v) of natamycin is present in solid form and the natamycin has an average particle diameter of at least 10 micrometers, and
  (iia) nisin is present in the product in an amount of 0.25 to 20 ppm, and wherein
 (b) if natamycin and nisin are applied on the product, then
  (ib) natamycin is present on the product in an amount of 0.01 to 7 ppm natamycin, wherein at least 90% (w/v) of natamycin is dissolved and/or less than 10% (w/v) of natamycin is present in solid form and the natamycin has an average particle diameter of at least 10 micrometers, and
  (iib) nisin is present on the product in an amount of 0.0001 to 1 ppm.

2. The process according to claim 1, wherein nisin and natamycin are added at the same time.

3. The process according to claim 1, wherein nisin and natamycin are present in an antimicrobial composition.

4. The process according to claim 1, wherein nisin and natamycin are applied at the surface of the product.

5. The process according to claim 1, wherein nisin and natamycin are applied by spraying or dipping.

6. The process according to claim 3, wherein the antimicrobial composition further comprises water and/or a salt and/or a component selected from the group consisting of a solvent, a surfactant, a carrier, a food acid, a thickener, and another food grade anti-microbial compound.

7. The process according to claim 1, wherein the product is selected from the group consisting of dairy products, ice cream mixes, spreads, margarines, sauce, and dressings.

8. A water-containing food product comprising at least about 82% moisture content and further comprising natamycin and nisin, wherein:
 (a) if natamycin and nisin are in the product, then
  (ia) natamycin is present in the product in an amount of 1 to 10 ppm natamycin based on the water content of the product, wherein at least 90% (w/v) of natamycin is dissolved and/or less than 10% (w/v) of natamycin is present in solid form and the natamycin has an average particle diameter of at least 10 micrometers, and
  (iia) nisin is present in the product in an amount of 0.25 to 20 ppm, or
 (b) if natamycin and nisin are present at a surface of the product, then
  (ib) natamycin is present at the surface of the product in an amount of 0.01 to 7 ppm natamycin, wherein at least 90% (w/v) of natamycin is dissolved and/or less than 10% (w/v) of natamycin is present in solid form and the natamycin has an average particle diameter of at least 10 micrometers, and
  (iib) nisin is present at the surface of the product in an amount of 0.0001 to 1 ppm.

9. The product according to claim 8, wherein the product is selected from the group consisting of dairy products, ice cream mixes, spreads, margarines, sauce, and dressings.

10. The product according to claim 9, wherein the product is a dairy product that is selected from the group consisting of cottage cheese, ricotta, cream cheese, sour cream and dairy desserts.

11. A process to preserve a water-containing food product comprising at least about 82% moisture content, the process comprising the step of applying natamycin and nisin in or on the product, wherein:
 (a) if natamycin and nisin are applied in the product, then
  (ia) natamycin is present in the product in an amount of 1 to 10 ppm natamycin based on the water content of the product, wherein at least 90% (w/v) of natamycin is dissolved and/or less than 10% (w/v) of natamycin is present in solid form and the natamycin has an average particle diameter of at least 10 micrometers, and
  (iia) nisin is present in the product in an amount of 0.25 to 20 ppm, and wherein
 (b) if natamycin and nisin are applied on the product, then
  (ib) natamycin is present on the product in an amount of 0.01 to 7 ppm natamycin, wherein at least 90% (w/v) of natamycin is dissolved and/or less than 10% (w/v) of natamycin is present in solid form and the natamycin has an average particle diameter of at least 10 micrometers, and
  (iib) nisin is present on the product in an amount of 0.0001 to 1 ppm;
 wherein the product produced by step (a) or (b) prevents growth of:
 (c) yeast and/or fungi for up to 6 weeks at temperatures ranging from 4 to 7° C.; and/or
 (d) yeast and/or bacteria for up to 3 months at temperatures ranging from 6 to 10° C.

12. The process of claim 11, wherein the product produced by step (a) or (b) prevents growth of:
 (c)(1) *Kluveromyces maxianus* or *Penicilliumroque forti* for up to 6 weeks at temperatures ranging from 4 to 7° C.

13. The process of claim 11, wherein the product produced by step (a) or (b) prevents growth of:
 (c)(2) *Listeria innocua* for up to 6 weeks at temperatures ranging from 4 to 7° C.

14. The process of claim 11, wherein the product produced by step (a) or (b) prevents growth of:
 (d)(1) *Lactobacilli* for up to 3 months at temperatures ranging from 6 to 10° C.

15. A water-containing food product comprising at least about 82% moisture content and further comprising natamycin and nisin, wherein:
 (a) if natamycin and nisin are in the product, then
  (ia) natamycin is present in the product in an amount of 1 to 10 ppm natamycin based on the water content of the product, wherein at least 90% (w/v) of natamycin is dissolved and/or less than 10% (w/v) of natamycin is present in solid form and the natamycin has an average particle diameter of at least 10 micrometers, and
  (iia) nisin is present in the product in an amount of 0.25 to 20 ppm, or
 (b) if natamycin and nisin are present at a surface of the product, then
  (ib) natamycin is present at the surface of the product in an amount of 0.01 to 7 ppm natamycin, wherein at least 90% (w/v) of natamycin is dissolved and/or less than 10% (w/v) of natamycin is present in solid form and the natamycin has an average particle diameter of at least 10 micrometers, and
  (iib) nisin is present at the surface of the product in an amount of 0.0001 to 1 ppm;
 wherein the product comprising natamycin and nisin prevents growth of:
 (c) yeast and/or fungi for up to 6 weeks at temperatures ranging from 4 to 7° C.; and/or
 (d) yeast and/or bacteria for up to 3 months at temperatures ranging from 6 to 10° C.

16. The water-containing food product comprising natamycin and nisin of claim 15, wherein the product prevents growth of:
   (c)(1) *Kluveromyces maxianus* or *Penicillium roqueforti* for up to 6 weeks at temperatures ranging from 4 to 7° C.

17. The water-containing food product comprising natamycin and nisin of claim 15, wherein the product prevents growth of:
   (c)(2) *Listeria innocua* for up to 6 weeks at temperatures ranging from 4 to 7° C.

18. The water-containing food product comprising natamycin and nisin of claim 15, wherein the product prevents growth of:
   (d)(1) *Lactobacilli* for up to 3 months at temperatures ranging from 6 to 10° C.

19. The process according to claim 1, wherein if natamycin and nisin are applied in the product, then natamycin is present in the product in an amount of 1 to 5 ppm.

20. The process according to claim 1, wherein if natamycin and nisin are applied on the product, then natamycin is present on the product in an amount of 0.1 to 5 ppm.

21. The process according to claim 1, wherein if natamycin and nisin are applied on the product, then natamycin is present on the product in an amount of 0.5 to 4 ppm.

22. The water-containing food product according to claim 8, wherein if natamycin and nisin are in the product, then natamycin is present in the product in an amount of 1 to 5 ppm.

23. The water-containing food product according to claim 8, wherein if natamycin and nisin are present at the surface of the product, then natamycin is present at the surface of the product in an amount of 0.1 to 5 ppm.

24. The water-containing food product according to claim 8, wherein if natamycin and nisin are present at the surface of the product, then natamycin is present at the surface of the product in an amount of 0.5 to 4 ppm.

* * * * *